United States Patent [19]

Gould et al.

[11] 4,451,635

[45] May 29, 1984

[54] POLYURETHANE QUATERNARY AMMONIUM SALTS

[75] Inventors: Francis E. Gould, Princeton; Christian W. Johnston, Neshanic Station, both of N.J.

[73] Assignee: Tyndale Plains-Hunter, Ltd., Princeton, N.J.

[21] Appl. No.: 355,938

[22] Filed: Mar. 8, 1982

[51] Int. Cl.$^3$ ............................................. C08G 18/42
[52] U.S. Cl. ....................................... 528/71; 528/59; 528/65; 528/73; 528/76; 528/80; 528/84; 528/44; 128/82; 128/155; 128/334 R; 128/334 C; 128/130; 128/132 D; 128/156; 424/78; 424/32; 351/160 R
[58] Field of Search ...................... 528/71, 59, 65, 73, 528/76, 80, 84, 44; 128/82, 155, 334 R, 334 C, 348, 130, 132 D, 156; 424/78, 32; 351/160

[56] References Cited

U.S. PATENT DOCUMENTS 4,255,550 3/1981 Gould .................................. 528/71

OTHER PUBLICATIONS

*Organic Chemistry*, by Morrison and Boyd, Allyn and Bacon, Inc., Jun. 1980, pp. 738–740 and 752–754.

*Primary Examiner*—John Kight, III
*Assistant Examiner*—M. L. Moore
*Attorney, Agent, or Firm*—Robert W. Kell; George F. Mueller

[57] ABSTRACT

Polyurethane quaternary ammonium salts are obtained by heating a solution of a polyurethane resin characterized by having present in the polymer backbone hydroxyl groups and at least one substituent selected from the group consisting of carboxylate radicals and carboxyl radicals dissolved in a water-miscible organic solvent for the resin at a temperature above 64° C. and below the decomposition temperature of said polyurethane resin with an organic chloride for a period of time; adding a strong base to the reaction mixture and continuing to heat said mixture to form a polyurethane quaternary ammonium hydroxide in solution; and precipitating the polyurethane quaternary ammonium hydroxide by pouring the reaction mixture into an excess of water. The polyurethane quaternary ammonium hydroxide so obtained may be dissolved in a solvent containing sufficient hydrochloric acid to bring the pH of the solution to 8; and the corresponding polyurethane quaternary ammonium chloride may be recovered from solution by evaporation of the solvent at a temperature below the decomposition point of the polyurethane quaternary ammonium chloride. A polyurethane quaternary ammonium sulfate may be prepared by dissolving in sulfuric acid a polyurethane resin characterized by having present in the polymer backbone hydroxyl groups and lactone groups to form a solution. This solution is added to an excess of water with stirring and neutralized with sodium hydroxide to bring the pH of the diluted solution to between 3 and 4. Evaporation of the solvent gives a residue containing a polyurethane quaternary ammonium sulfate and sodium sulfate. The polyurethane quaternary ammonium sulfate may be separated from the mixture by extraction with methanol.

2 Claims, No Drawings

POLYURETHANE QUATERNARY AMMONIUM SALTS

This invention relates to hydrophilic polyurethane quaternary ammonium salt compositions. More particularly, the present invention relates to compositions obtained by the reaction of a solution of one or more organic chlorides and one or more hydrophilic polyurethane resins dissolved in a water-miscible organic solvent in the presence of a strong base.

The hydrophilic polyurethanes that are employed as the starting material of the present invention may be made by the reaction of:

(A) one or more diols having a number average molecular weight in the range of from about 200 to 200,000, selected from the group consisting of:

(a) diethylene glycol, and
(b) long-chain polyoxyalkylene diols, with (B) a reactant selected from the group consisting of organic polyisocyanates and nitrile carbonates, and (C) a polyfunctional lactone having the formula:

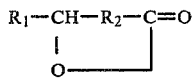

wherein $R_1$ is a monovalent radical selected from the group consisting of $-H$, $-CH_2NH_2$, $-SO_2CH_3$, and $-(CHOH)_nCH_2OH$; n being an integer from 0 to 5; and $R_2$ is a divalent radical $-(-CHOH)_m-$; m being the integer from 2 to 10; and ethers derived from said lactones. The reaction of components (A), (B) and (C) above is carried out in the presence of an organic tin catalyst and the amount of the component (C) that is present may vary from about 0.1% to about 30% of the weight of the total reaction mixture. Polyurethane resins containing such polyfunctional lactones are described in U.S. Pat. Nos. 4,156,066 and 4,156,067.

The hydrophilic polyurethane component which is reacted with an organic chloride contains diethylene glycol and a long-chain water-soluble diol. The long-chain, water-soluble diols should have a molecular weight of at least about 200 and preferably 1450 to 7500 and may be derived from ethers, i.e., ethylene oxide and propylene oxide. Suitable diols consist predominantly of oxyethylene or oxypropylene groups, though a minor proportion of other oxyalkylene groups may be included.

The polyisocyanate used to make the hydrophilic polyurethane component of the present invention may be represented by $R(NCO)_n$ wherein n is greater than 1, preferably 2–4, and R is an aliphatic, alicyclic, aliphatic-alicyclic, aromatic, or aliphatic-aromatic hydrocarbon compound of from 4 to 26 carbon atoms, but more conventionally from 6 to 20 and generally from 6 to 13 carbon atoms. Representative examples of the above isocyanates are: tetramethylene diisocyanate; hexamethylene diisocyanate; trimethylhexamethylene diisocyanate; dimer acid diisocyanate; isophorone diisocyanate; diethylbenzene diisocyanate; decamethylene 1,10-diisocyanate; cyclohexylene 1,2-diisocyanate and cyclohexylene 1,4-diisocyanate and the aromatic isocyanates such as 2,4- and 2,6-tolylene diisocyanate; 4,4'-diphenylmethane diisocyanate; 1,5-naphthalene diisocyanate; dianisidine diisocyanate; tolidine diisocyanate; a polymeric polyisocyanate such as neopentyl tetra isocyanate; m-xylene diisocyanate; tetrahydronaphthalene-1,5 diisocyanate; and bis(4-isocyanatophenyl) methane.

The preferred isocyanate is methylene di(cyclohexyl isocyanate). Other but slightly less preferred diisocyanates are trimethyl hexamethylene diisocyanate and isophorone diisocyanate.

Other compounds which are useful are the isocyanate equivalents which produce the urethane linkages such as the nitrile carbonate, i.e., the adiponitrile carbonate of the formula:

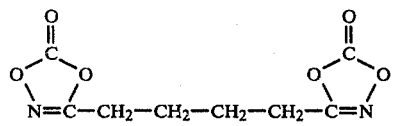

In the manufacture of the hydrophilic polyurethane resin component of this invention, low molecular weight glycols such as diethylene glycol and dipropylene glycol or an aromatic polyol may be added to the reaction mixture. The preferred low molecular weight aromatic polyols are bisphenol A and 4,4'-sulfonyldiphenol.

The proportions in which the long-chain polyglycol and the low molecular weight glycol, i.e., diethylene glycol are present in the hydrophilic polyurethane component of this invention depends on the hydrophobic-hydrophilic balance present in each and desired in the final composition. Increasing the molecular weight of the long-chain polyoxyethylene glycol and/or the amount of this polyol contributes strong hydrophilic properties to the final product. This effect may be counterbalanced by increasing the proportion of low molecular weight glycol, i.e., diethylene glycol or dipropylene glycol or polypropylene glycol.

Keeping the above in mind (that it is the number of polyethylene oxide groups in the polymer molecular that determines hydrophilic properties and that the polyethylene oxide groups are more hydrophilic than are polypropylene oxide groups), it is a simple matter to choose mixtures of reactants such that the hydrophilic polyurethane resin to be converted into the desired quaternary ammonium salt will have the desired properties. By choosing the molecular weight of the polyethylene glycol or using two polyalkylene glycols of different molecular weight one may "tailor make" the hydrophilic polyurethane component to satisfy a wide range of properties. It will be understood that the term "hydrophilic polyurethanes" as used throughout the specification and claims is used to describe the polyurethane resins that are converted to the corresponding quaternary ammonium salts. Such "hydrophilic polyurethanes" will take up at least 20 weight percent water when immersed in water and form hydrogels through hydrogen bonding.

As mentioned above, the hydrophilic polyurethane resin that is reacted with an organic chloride and a strong base to form the polyurethane quaternary ammonium salts of the present invention will contain from about 0.1 to about 30 weight percent of a polyfunctional lactone. Representative examples of the polyfunctional lactones are those derived from polysaccharides and monosaccharides such as mannolactone, delta gluconolactone, sorbolactone and D-glycuronolactone.

It is desirable that the lactones employed have at least 3 and preferably 4 or more hydroxyl groups in the molecule or at least 1 more than is required to form a linear polyurethane chain. These free (unreacted) hydroxyl groups remain in the polymer backbone and are available for crosslinking the polymer. The lactone ring is also reactive and is opened, i.e., by hydrolysis, prior to or during the formation of the quaternary ammonium salt to form carboxylate groups (COONa) or carboxyl groups (COOH) in the polymer backbone.

In making the hydrophilic polyurethane component, the glycols are mixed with the lactone and the polyisocyanate is reacted with the mixture although other techniques may be used. The reaction is catalyzed by known catalyst for such reaction, suitable ones being tin salts and organic tin esters such as dibutyl tin dilaurate, tertiary amines such as triethyl diamine (DABCD), N,N,N',N'-tetramethyl-1,3-butane diamine and other recognized catalyst for urethane reactions which are well known in the art. The reaction can be conducted in the absence or presence of diluent or solvent.

In preparing the hydrophilic polyurethane quaternary ammonium salts of the present invention, one or more polyurethanes having hydroxyl groups are dissolved and heated in a miscible organic solvent such as methanol or 95% ethanol with an organic chloride. A strong base is added to the reaction mixture and heating is continued at a temperature above the boiling point of the organic liquid but below the decomposition point of the polyurethane resin to form a polyurethane quaternary ammonium hydroxide. The quaternary ammonium hydroxide may be precipitated by pouring the reaction mixture into an excess of water.

Although the quaternary ammonium hydroxide is insoluble in methanol, it may be dissolved in methanol containing sufficient hydrochloric acid to lower the pH to 2.0. After acidification, the resin will no longer precipitate from methanol when added to an excess of water. The polyurethane quaternary ammonium chloride may be recovered from solution by heating under reduced pressure to drive off the solvent.

In accordance with the present invention, a polyurethane quaternary ammonium salt characterized by having present in the polymer backbone hydroxyl groups and at least one substituent selected from the group consisting of carboxylate and carboxyl radicals was prepared by dissolving in a water-miscible organic solvent one or more of the hydrophilic polyurethane resins discussed above and an organic chloride. This reaction mixture was heated with agitation to a temperature above 64° C. but below the decomposition temperature of the resin in the presence of a strong base to form a polyurethane quaternary ammonium hydroxide in solution.

The polyurethane quaternary ammonium hydroxide was recovered from solution by pouring the reaction mixture into an excess of water and isolating the precipitate that was formed.

The polyurethane quaternary ammonium hydroxide so obtained may be converted into the corresponding polyurethane quaternary ammonium chloride by dissolving it in water or a water-miscible organic solvent containing sufficient hydrochloric acid to bring the pH to 2.0. The polyurethane quaternary ammonium chloride may then be recovered from solution by evaporation of the solvent at a temperature below the decomposition temperature of the quaternary ammonium salt.

Other polyurethane quaternary ammonium salts, namely, polyurethane quaternary ammonium sulfates may be prepared by dissolving a hydrophilic polyurethane resin in sulfuric acid. This solution is then poured into an excess of water, neutralized to pH 3.5 with aqueous sodium hydroxide, filtered and evaporated to dryness. The residue is a mixture of sodium sulfate and polyurethane quaternary ammonium sulfate. The polyurethane ammonium sulfate may be extracted from the residue with methanol.

The organic chloride that is employed in the present invention may be any active organic chloride containing from about 2 to about 10 carbon atoms in the molecular and may be an aryl, arylalkyl or alkyl chloride such as chlorobenzene, benzyl chloride or butyl chloride. Particularly preferred are the more reactive chlorides such as alkyl chloride and methallyl chloride.

The water-miscible organic solvent that is used as a reaction medium in the present invention may be any water-miscible organic solvent, preferably a polar water-miscible organic solvent, for the polyurethane resin and organic chloride. The solvent should have a boiling point above about 64° C. and lower than the decomposition temperature of the polyurethane resin. Particularly preferred are the low molecular weight alcohols and polyols such as methanol, ethanol, ethylene glycol, glycerol, etc.

The reaction of the hydrophilic polyurethane resin with an organic chloride to form a polyurethane quaternary ammonium salt will not proceed in the absence of a strong base. Suitable bases for this reaction are the alkali metal hydroxides such as sodium hydroxide and potassium hydroxide. The anion that is associated with the polyurethane quaternary ammonium salt is pH dependent and will be the hydroxyl ion when the pH is high (pH 10 or above). When the pH is reduced to about 2 with hydrochloric acid, the anion is the chloride ion.

The hydrophilic polyurethane quaternary ammonium salts of the present invention are soluble in water (or in water containing a small amount, e.g., 5% methanol, ethanol or propanol. It is, therefore, possible to make an aqueous solution of the hydrophilic polyurethane quaternary ammonium salt that is essentially free of organic solvents and apply coatings from solution while avoiding the fume and fire hazards that may occur when organic solvents are present.

The hydrophilic polyurethane quaternary ammonium salts of the present invention are also useful as molding compounds, absorbents, controlled release agents, ion exchange resins, and in the manufacture of dialysis membranes, dentures, cannulae, contact lenses, packaging components, burn dressings, contraceptive devices, sutures, surgical implants, blood oxygenators, intrauterine devices, vascular protheses, oral delivery systems, battery separator plates, eye bandages, antifog coatings, surgical drapes, oxygen exchange membranes, artificial finger nails, finger cots, adhesives, gas permeable membranes, and in protective and drag resistant coatings.

The practice of the invention is further illustrated by the following examples without being restricted thereto, the parts being by weight, unless otherwise stated.

EXAMPLE I

A diethylene glycol solution of polyethylene glycol was prepared by heating 477.6 g (0.329 mole) of polyethylene glycol having a molecular weight of 1,450 in 62.7 g (0.591 mole) of diethylene glycol and 2.4 g of water with stirring. The solution, which was heated to 80° C. during the melting of the ingredients was cooled to below 60° C. and to it was added a mixture of 44.9 g (0.252 mole) of delta gluconolactone dispersed in 320.3 g (1.213 moles) methylene biscyclohexyl-4,4'-isocyanate (a product identified as DESMODURE W sold by Mobay Chemical Corporation, Pittsburgh, Pa.). Stirring was continued while the batch continued to cool. One and eight-tenths grams by weight of an organic tin catalyst, dibutyl tin dilaurate, (a product identified as $T_{12}$ manufactured by Metal and Thermit Company of Rahway, N.J.) was added to the reaction mixture with stirring at a temperature below 45° C. to avoid undue temperature rise caused by the heat of reaction. Stirring was contined after addition of the catalyst. The reaction mixture first became clear and as the temperature reached 80° C. over 1–2 minutes, it began to foam. The foamed reaction mixture was then poured into a polypropylene pan and placed in an oven at 100° C. for 15 minutes.

The foamed resin after heat curing and cooling to room temperature was cut into small pieces and 869 g of this foamed resin was added with stirring to 3,480 g of methanol and permitted to swell. Rapid stirring was commenced and continued during the addition of 119.7 parts of a 20% aqueous solution of sodium hydroxide. After about an hour of stirring, the resin dissolved in the alkaline methanol solution. The pH of the solution was adjusted to pH 8.8 with 10% HCl solution. This resin solution was then centrifuged to remove any suspended solids and added slowly with stirring to a large quantity of water (10,400 ml). The resin precipitated from the water solution as a taffy-like solid. Stirring was continued for 30 minutes after the addition of the last of the resin solution. The resin was separated from the water, comminuted by grinding, and the comminuted resin was given a second wash by stirring in 12,000 ml of water. The small particles of resin after washing for a second time are spread on a polypropylene screen and dried at room temperature. The polyurethane resin so obtained has present in the polymer backbone hydroxyl groups and depending on the pH of the resin solution prior to precipitation of the resin, either carboxyl groups (—COOH) carboxylate groups (COONa) or both carboxylate and carboxyl groups.

EXAMPLE II

Twenty grams of the polyurethane resin prepared as described in Example I above was dissolved in methanol. The solids content was 9.77%. To 69.18 ml of this solution was added 2.13 g of chlorobenzene with stirring and the mixture was refluxed (with stirring) for 4 hours. To this mixture was added 0.818 g of sodium hydroxide and stirring and refluxing was continued another 4 hours. The solution was allowed to stand overnight and a finely divided sediment that formed upon standing was removed by filtration. The filtered solution was poured into one liter of distilled water to form a precipitate. This precipitate was the quaternary ammonium hydroxide salt of the polyurethane resin. The precipitate was separated from the water as a wet mass weighing 20.3 g. This wet mass as insoluble in methanol. However, it dissolved in 450 ml of methanol containing sufficient hydrochloric acid to lower the pH to 2.0. After acidification, the resin no longer precipitated when the methanol solution was added to an excess of water. The resin was isolated as a solid (5.2 g) by heating at 95° C. to drive off the solvents. The dry resin so obtained was no longer water soluble but was soluble upon stirring in water containing 5 weight percent methanol.

The solid resin (5.2 g) was a polyurethane resin quaternary ammonium chloride and analyzed 3.06% carbonyl group, by titration. There is present in the polymer backbone of this resin hydroxyl groups and at least one substituent selected from the group consisting of carboxylate radicals and carboxyl radicals.

EXAMPLE III

A resin was prepared as described above in Example I from the following reagents:

| | | |
|---|---|---|
| Polyglycol Molecular wt. 1450 | 386.1 g | (0.266 mole) |
| Diethylene glycol | 61.8 g | (0.582 mole) |
| Water | 1.8 g | |
| Delta gluconolactone | 109.0 g | (0.612 mole) |
| DESMODURE W | 349.3 g | (1.323 moles) |
| | 908.0 g | |
| Catalyst $T_{12}$ | 1.8 g | |

The resin after heating at 100° C. for 15 minutes contained hydroxyl and lactone groups in the polymer backbone. This resin was cut into small pieces and added with stirring to 3,300 parts of methanol. The resin swelled in the methanol solution and 148.8 g of a 20% aqueous sodium hydroxide solution was added with continued stirring. After 1 hour, the resin had dissolved. The resin solution was centrifuged to remove suspended solids and added to a large volume of water with stirring. The resin precipitated as a taffy-like solid. After stirring for an additional one-half hour, the resin was taken out of solution and cut into small pieces. The comminuted resin was given a second wash by stirring with water and the small particles of resin were spread on a screen to dry. The polyurethane resin so obtained was characterized by having present in the polymer backbone hydroxyl groups and either carboxylate or carboxyl radicals or a mixture of carboxylate and carboxyl radicals derived from splitting the lactone ring.

EXAMPLE IV

To 13.76 g of the polyurethane resin described above in Example III was added 55.05 g of methanol and the mixture was refluxed for 2 hours with 3.58 g of chlorobutane. To this mixture was added 1.469 g of sodium hydroxide and refluxing was continued for another 2 hours. The mixture was permitted to stand overnight and the solution so obtained was poured into 1,000 parts of water to precipitate a taffy-like resin. The material recovered weighed 39.5 parts. The quaternary ammonium hydroxide resin so obtained was dissolved in 350 g of methanol containing sufficient HCl to bring the pH to 8. No precipitate formed when the methanol solution was added to water. Evaporation of the water at 55° C. gave a resin residue weighing 11.0 parts. This resin was soluble in methanol and water containing 5 weight percent methanol. If evaporated to near dryness, the resin is soluble in water. This Example illustrates the preparation of a polyurethane resin quaternary ammonium hydroxide in the presence of chlorobutane, and conversion of the quaternary ammonium hydroxide obtained to the corresponding quaternary ammonium chloride.

EXAMPLE V

Fifty grams of a polyurethane polyether resin prepared as described above in Example IV was added to 500 ml of an aqueous solution containing 17.4 ml of 29% ammonium hydroxide. The solution was stirred at 40° C. until all of the polymer dissolves. To the polymer solution at room temperature was added 10 ml of an aqueous 20% solution of potassium dichromate [2.0 g $(NH_4)_2Cr_2O_7$]. The solution was applied to cellulose acetate film with a doctors knife and dried at room temperature in subdued light or darkness. A tough film of the photosensitive polymer, light yellow in color, was deposited that adhered well to the cellulose acetate substrate. A photographic image was projected onto the film using an actinic lamp, e.g., a No. 2 photoflood lamp, as the light source and an exposure time of 60 seconds. The film was developed by washing in water at room temperature to dissolve and remove the unexposed and uncross-linked portion of the photographic image. Since the polymer that formed the photographic image was substantive to ink, the developed film may be used in a lithography printing process.

The resin of Example IV when deposited in this manner as a film, produced a very sharp image upon exposure to light. The unexposed area was easily cleared by washing with water.

EXAMPLE VI

To 164.4 g of a resin prepared as described in Example II above, dissolved in sufficient methanol to obtain 26.99% solids, was added 8.1 g of chlorobenzene and the mixture was agitated at 65° C. for 2 hours. The pH of this solution was 10.5. After cooling, sufficient sodium hydroxide was added to increase the pH to 12.5. The mixture was refluxed an additional 2 hours and allowed to stand overnight. The solution so obtained was poured into 2,800 ml of water and no precipititate formed. On prolonged heating for 2 hours at 35° C.-40° C., the solubility of the resin decreased and agglomerates formed and rose to the surface. The resin was separated from the water and air dried. This Example illustrates the preparation of a polyurethane resin quaternary ammonium chloride prepared in the presence of chlorobenzene.

EXAMPLE VII

A solution of 301.4 g of the resin described in Example III above and 80.9 g of methanol were refluxed for 2 hours at 62° C. with 13.89 g of 1-chlorobutane. The reaction mixture was cooled and 34.96 g of sodium hydroxide was added. The reaction mixture was agitated with a magnetic stirrer until the caustic was dissolved and refluxed for 2 hours at 64° C. After standing overnight, the pH of the reaction mixture was 12.0. The pH was reduced to 2.3 by the addition of hydrochloric acid (100 g of 37.2% HCl) agitated a half-hour and allowed to settle. Sodium chloride precipitated from the solution and was removed by filtration. The clear solution was air dried to give a resin that was soluble in water at a temperature of 35° C.-40° C. Higher temperature reduced the solubility; at 80° C. the polymer was precipitated from solution but went back into solution when the temperature was dropped to 35° C.

This polyurethane quaternary ammonium chloride resin may be formulated as described above in Example V with ammonium dichromate to prepare a solution of photosensitive hydrophilic polymer that may be applied to a boat hull and converted by ambient light to a water insoluble cross-linked hydrophilic polymer. This polymer coating will improve the drag resistance of the boat and control the release of anti-fouling agents that may have been previously applied to the boat or incorporated in the coating composition.

EXAMPLE VIII

Fifty grams of the polyurethane quaternary ammonium chloride made as described above in Example II is added to 500 ml of an aqueous solution containing 17.4 ml of 29% ammonium hydroxide. The solution obtained is filtered and 4 g of ammonium dichromate is dissolved in the filtered solution. The solution is applied to a MYLAR ® film with a doctors knife and dried at room temperature in subdued light or darkness. A tough film of the photosensitive polymer, light yellow in color, is deposited that adheres well to the MYLAR ® substrate. A photographic image is projected onto the film using a S-1 sunlamp as the light source and an exposure time of 60 seconds. The film is developed by washing in water at room temperature to dissolve and remove the unexposed and uncross-linked portion of the photographic image.

EXAMPLE IX

A hydrophilic polyurethane resin was made as described in Example II above from the following:

| | |
|---|---|
| Polyethylene Glycol (Mol. wt. 1450) | 42.52 g |
| Diethylene Glycol | 6.80 g |
| Water | 0.20 g |
| Delta Gluconolactone | 12.01 g |
| DESMODURE W | 38.47 g |
| | 100.00 |
| Catalyst $T_{12}$ | 0.2 g |

The polyethylene glycol, diethylene glycol and water were melted together at 80° C. with stirring, cooled to below 60° C. and the delta gluconolactone and DESMODURE W were stirred together and added to the polyol mixture which further reduced the temperature. The catalyst was added with continued stirring as described in Example I above and the foamed reaction mixture was placed in an oven at 100° C. for 15 minutes. The polyurethane resin so obtained has hydroxyl groups and lactone groups in the polymer backbone.

EXAMPLE X

The resin described above in Example IX was cut into small pieces (2 cm × 1 cm) and 6.82 g of this resin were added over 10 minutes with stirring to 50 g of 90% sulfuric acid. The acid was warmed and agitated. The reaction mixture foamed, some of the resin dissolved and the solution become red brown. The reaction mixture was allowed to set overnight and the next day all resin had dissolved. When this solution was violently stirred, it developed a head of foam.

This solution was slowly added to 1,000 ml of water. Nothing precipitated. After two hours, the solution was neutralized with an aqueous 20% sodium hydroxide solution to a pH of 3.5. A precipitate formed upon standing for 2 hours. The solution was filtered and the precipitate was dissolved in methanol and re precipitated from water to obtain about 0.8 g of resin. The clear filtrate was evaporated to dryness and gave a residual of sodium sulfate crystals and a small amount of resin. The residual resin was washed from the sodium sulfate with dry methanol which on evaporation yielded 3.18 g of resin. This resin on examination showed 8.36% $SO_4^-$ or 0.871 millimoles of $SO_4^-/g$ of resin, and is consistent with a polyurethane quaternary ammonium sulfate characterized by hydroxyl groups and at least one radical selected from the group consisting of carboxylate radicals and carboxyl radicals in the polymer backbone.

Ten grams of this resin (analyzing 8.36% SO$_4$) was dissolved in 90 grams of ethanol and to 100 grams of this solution was added with stirring 4 g of a 20 weight percent aqueous ammonium dichromate solution. The solution was spread on a release surface and the solvent evaporated to form a film which was cured in ambient light. The resulting film, when removed, was an excellent ion exchange membrane.

EXAMPLE XI

A polymer was made based on the following composition:

| | |
|---|---|
| Polyethylene Glycol | 52.60 g |
| Diethylene Glycol | 6.91 g |
| Water | 0.26 g |
| Delta Gluconolactone | 4.95 g |
| DESMODURE W | 35.28 g |
| | 100.00 |
| Catalyst T$_{12}$ | 0.20 g |

The first three ingredients were melted together to form a clear solution at a temperature below 80° C. The mixture was allowed to cool to 55° C. and a dispersion of finely divided delta gluconolactone and DESMODURE W in the amounts shown above were added to the melted polyols. This cooled the mass to about 45° C. At this point, the catalyst was added and the temperature rose slowly at first and then more rapidly. As the temperature reached 80° C., the mass developed some foam and was transferred to a polypropylene tray and placed in the oven at 100° C. for one hour.

After removing from the oven and cooling, the foamed material was cut into ¾ inch cubes. Five hundred grams of these cubes were placed in 3,000 g of methanol and permitted to swell with stirring for one-hour. Sodium hydroxide (86 g) was then added as a 20% solution, and the mixture was strongly agitated until the resin dissolved. The pH was then adjusted to 8.8 with a 10% hydrochloric acid solution and poured with stirring into an excess of water (18,000 ml) to precipitate the resin. The precipitate was cut into small pieces and washed in a similar additional quantity of water. The resin was recovered and placed on a screen to dry. There is present in the polymer backbone of this resin hydroxyl groups and at least one substituent selected from the group consisting of carboxylate radicals and carboxyl radicals.

EXAMPLE XII

The dried resin from Example XI above (93.08 g) was dissolved in 372 g of methanol to give 465 g of a solution to which was added, with stirring a mixture of

| | |
|---|---|
| Sulfuric Acid (96.5%) | 15.17 g |
| Water | 6.30 g |
| Methanol | 10.00 g |

Upon addition of the sulfuric acid mixture a light bubbling was observed. The reaction mixture was agitated, slightly warmed and allowed to sit overnight. The next day, 9.8 g of 20% sodium hydroxide was added to bring the pH between 3 and 4. The resultant cloudy solution was filtered.

A resin was precipitated by pouring this alcoholic filtrate into 2,280 ml of water. The precipitated polymer was washed by dispersing in 2,280 ml water with stirring. A second washing of the precipitate polymer (in 2,280 ml of water) dissolved it. The 2,280 ml of water used to precipitate the resin and the two wash waters were evaporated to yield 24.2, 29.1 and 35.8 g of resin, respectively. As the water evaporated, the solution became milky and the recovered polymer although not water soluble was hydrophilic. The combined polymers recovered upon evaporation had a yellow color with a green image and analyzed, upon ignition, 5.02% sulfur as (SO$_4^-$).

Two grams of this material was dissolved in 18 g of ethanol and 0.8 g of an aqueous 20% ammonium dichromate solution was added. This mixture was applied to a MYLAR ® film to form a photosensitive coating. The film showed good photosensitivity. The exposed parts clung tenaciously to the film and the unexposed parts were easily washed away.

EXAMPLE XIII

One hundred grams of the polyurethane quaternary ammonium salt prepared as described in Example II was milled with 3.8 grams of finely divided calcium oxide until thorough mixing had occurred. The resin mixture was then placed in a mold shaped to produce contact lens and cured at a temperature of 210° C. and pressure of 27,579 kPa (4,000 psi) for 5 minutes.

EXAMPLE XIV

Four milligrams iodine is added to a solution of 800 mg of the polyurethane resin quaternary ammonium chloride prepared in Example II in 3,300 mg of ethyl alcohol (95%) and 700 mg water. The mixture is stirred with a magnetic stirrer during one hour and a layer of the homogeneous alcoholic solution was spread with an applicator having a 0.254 mm (10 mil) clearance on a horizontal casting table lined with polyethylene film which had been washed with benzene and alcohol. The film is allowed to dry at room temperature and the dried film was placed under reduced pressure for another 4 hours. The resulting dry film is 0.5 mm (20 mils) thick and is permeable to gases. It may be cut into any desired shape. The film may be used as a burn dressing and the slow release of iodine provides a barrier against infection.

EXAMPLE XV

One hundred grams of the polyurethane quaternary ammonium chloride prepared as described in Example II was milled with 4 grams of finely divided calcium oxide and 2 grams of lactic acid until thorough mixing had occurred. The resin mixture was then placed in a mold shaped to form an interuterine device and cured at a temperature of 215° C. and pressure of 27,579 kPa (4,000 psi) for 5 minutes.

EXAMPLE XVI

Two grams of the polyurethane ammonium chloride described in Example IV above; 100 mg of Norethandrolone (NILEVAR) and 30 mg of finely divided calcium oxide are milled together until thorough mixing had occurred. The resin mixture was then placed in a mold shaped in the form of a cylinder and cured at a temperature of 215° C. and a pressure of 27,579 kPa (4,000 psi) for 5 minutes. After removing from the mold, a cylinder suitable for in vivo implantation to provide prolonged release of Norethandrolone is obtained for use in animal husbandry.

In a similar manner, an antibiotic such as penicillin or a steroid composition may be substituted for the Norethandrolone to obtain slow release of penicillin into a body cavity.

EXAMPLE XVII

Fifty grams of the polyurethane quaternary ammonium chloride described above in Example II is added to 500 ml of an aqueous solution containing 40 ml of methanol, 2 g of iodide and 29% ammonium cloride. To this solution is added 80 parts of ammonium dichromate and the mixture is stirred until the ammonium dichromate dissolves.

A cannula woven of cotton fibers is immersed in this solution to thoroughly wet the fabric. The coated cannula is removed from the solution and exposed to the sun while drying. The resulting product will retain its shape and an open lumen after flexing.

EXAMPLE XVIII

The ammonium dichromate catalyzed solution of polyurethane quaternary ammonium chloride described above in Example XVII was applied to the exterior surface of a vascular prosthesis of woven nylon strands and was permitted to air dry in direct sunlight. This step was repeated four times over a period of time sufficient to permit the complete drying and curing of successive coatings to fill the interstacies between the woven nylon strands and provide a vascular prosthesis having a smooth exterior surface.

EXAMPLE XIX

One hundred grams of the polyurethane quaternary ammonium chloride described in Example II above was milled with 3.8 g of a finely divided calcium oxide and 5 g of sulfadiazine until thoroughly mixed. The mixture was molded at 210° C. under 27,579 kPa pressure (4,000 psi) to form an oral delivery system that will slowly release sulfadiazine following ingestion.

EXAMPLE XX

One hundred grams of the polyurethane quaternary ammonium salt described above in Example II was milled with 4 grams of a finely divided calcium oxide until thoroughly mixed. The mixture was molded at 220° C. and 27,579 kPa (4,000 psi) to form a battery separator plate measuring 10 cm × 4 cm × 0.5 cm.

EXAMPLE XXI

Two hundred grams of the polyurethane quaternary ammonium chloride described above in Example IV was milled with 10 grams of finely divided calcium oxide until thoroughly mixed and then extruded through an annular orifice at 220° C. under 20,684 kPa (3,000 psi) to form a tube having an internal diameter of 0.3 cm and a wall thickness of 60 mm. A piece of this tube three meters in length is immersed in water and dry nitrogen is passed through the tube at the rate of 50 cc per minute for one hour. The dry nitrogen picked up moisture as it passed through the tube.

EXAMPLE XXII

An anti-fouling marine paint is formulated by grinding in a vented ball mill for 3 hours in the presence of dry ice:

| | |
|---|---|
| Polyurethane Quaternary Ammonium Chloride of Ex. VII | 150 g |
| 5% Ammonium Hydroxide in Ethanol | 500 g |
| Potassium Dichromate | 2 g |
| Wolastinite | 50 g |
| Mercury Acetate | 3 g |

The product so obtained may be applied to wood and other surfaces to form a film that is cross-linked by sun light to form an adherent insoluble protective coating. The product is particularly effective when applied to the hull of a boat as the cured coating slowly releases mercuric acetate and prevents barnacle or algae formation on the painted surfaces.

EXAMPLE XXIII

A diethylene glycol solution of polyethylene glycol was prepared by heating 477.6 g (0.329 mole) of polyethylene glycol having a molecular weight of 1,450 in 62.7 g (0.591 mole) of diethylene glycol with stirring. The solution which was heated to 80° C. during the melting of the ingredients was cooled to below 60° C. and to it was added a mixure of 44.9 g (0.252 mole) of delta gluconolactone dispersed in 320.3 g (1.213 moles) methylene biscyclohexyl-4,4'-isocyanate (a product identified as DESMODURE W sold by Mobay Chemical Corporation, Pittsburgh, Pa.). Stirring was continued while the batch continued to cool. One and eight-tenths grams by weight of an organic tin catalyst, dibutyl tin dilaurate, (a product identified as $T_{12}$ manufactured by Metal and Thermit Company of Rahway, N.J.) was added to the reaction mixture with stirring at a temperature below 45° C. to avoid undue temperature rise caused by the heat of reaction. Stirring was continued after addition of the catalyst. The reaction mixture first became clear and as the temperature reached 80° C. over 1-2 minutes, it began to foam. The foamed reaction mixture was then poured into a polypropylene pan and placed in an oven at 100° C. for 15 minutes.

The foamed resin, after heat curing and cooling to room temperature, was cut into small pieces and 869 g of this foamed resin was added with stirring to 3,480 g of methanol and permitted to swell. Rapid stirring was commenced and continued during the addition of 119.7 parts of a 20% aqueous solution of sodium hydroxide. After about an hour of stirring, the resin dissolved in the alkaline methanol solution. The pH of the solution was adjusted to pH 8.8 with 10% HCl solution. This resin solution was then centrifuged to remove any suspended solids and added slowly with stirring to a large quantity of water (10,400 ml). The resin precipitated from the water solution as a taffy-like solid. Stirring was continued for 30 minutes after the addition of the last of the resin solution. The resin was separated from the water, comminuted by grinding, and the comminuted resin was given a second wash by stirring in 12,000 ml of water. The small particles of resin, after washing for a second time, are spread on a polypropylene screen and dried at room temperature.

This resin may be converted into a quaternary ammonium salt by the procedure described in Example II above.

EXAMPLE XXIV

Fifty grams of quaternary ammonium salt made from the polyurethane resin of Example XXIII by the method described in Example II was added to 500 ml of an aqueous solution containing 17.4 ml of 29% ammonium hydroxide. The solution was stirred at 40° C. until all of the polymer dissolves. To the polymer solution at room temperature was added 10 ml of an aqueous 20% solution of potassium dichromate [2.0 g $(NH_4)_2Cr_2O_7$]. The solution was applied to a sheet of glass with a doctors knife and dried in the sunlight. The coated surface was resistant to fogging when the sheet of glass was moved from a cold area into a warm and humid room.

We claim:

1. A water soluble polyurethane quaternary ammonium salt characterized by having present in the polymer backbone hydroxyl groups and at least one substituent selected from the group consisting of carboxylate radicals and carboxyl radicals and the anion is a chloride ion.

2. A water soluble polyurethane quaternary ammonium salt characterized by having present in the polymer backbone hydroxyl groups and at least one substituent selected from the group consisting of carboxylate radicals and carboxyl radicals and the ion is a sulfate ion.

* * * * *